United States Patent [19]
Mayzels et al.

[11] Patent Number: 5,269,791
[45] Date of Patent: Dec. 14, 1993

[54] SURGICAL KNOT PUSHING APPLIANCE

[76] Inventors: Ilya Mayzels, 2451 Coldwater Cyn Dr., Beverly Hills, Calif. 90210; Joseph Shvager, 10847 Wystone Ave., Northridge, Calif. 91326

[21] Appl. No.: 958,906

[22] Filed: Oct. 9, 1992

[51] Int. Cl.$^5$ .............................................. A61B 17/00
[52] U.S. Cl. ........................................ 606/148; 606/1; 606/139; 606/144
[58] Field of Search ............... 606/1, 126, 106, 108, 606/110, 139, 144, 148; 604/264, 282; 128/772

[56] References Cited

U.S. PATENT DOCUMENTS

| | | | |
|---|---|---|---|
| 1,063,750 | 6/1913 | Townsend | 606/126 |
| 3,687,138 | 8/1972 | Jarvik | 606/139 |
| 4,018,229 | 4/1977 | Komiya | 606/139 |
| 4,653,496 | 3/1987 | Bundy et al. | 604/264 |
| 4,683,885 | 8/1987 | Hutterer et al. | 606/1 |
| 4,936,306 | 6/1990 | Doty | 128/731 |
| 5,054,501 | 10/1991 | Chuttani et al. | 604/282 |
| 5,192,295 | 3/1993 | Danforth | 128/772 |
| 5,197,482 | 3/1993 | Rank et al. | 604/264 |

FOREIGN PATENT DOCUMENTS 0923530  5/1982  U.S.S.R. .............................. 606/148

Primary Examiner—Stephen C. Pellegrino
Assistant Examiner—Jeffrey A. Schmidt
Attorney, Agent, or Firm—David O'Reilly

[57] ABSTRACT

A surgical knot pushing tool comprised of a spiralling coil on the tip of an elongate shaft. The spiralling coil is preferably conically tapered and has the respective coils spaced to receive a surgical thread. The conically tapered coil narrows to an opening at the end that is slightly larger than the diameter of surgical thread but is small enough to prevent a surgical knot from slipping off the knot pushing tool.

3 Claims, 1 Drawing Sheet

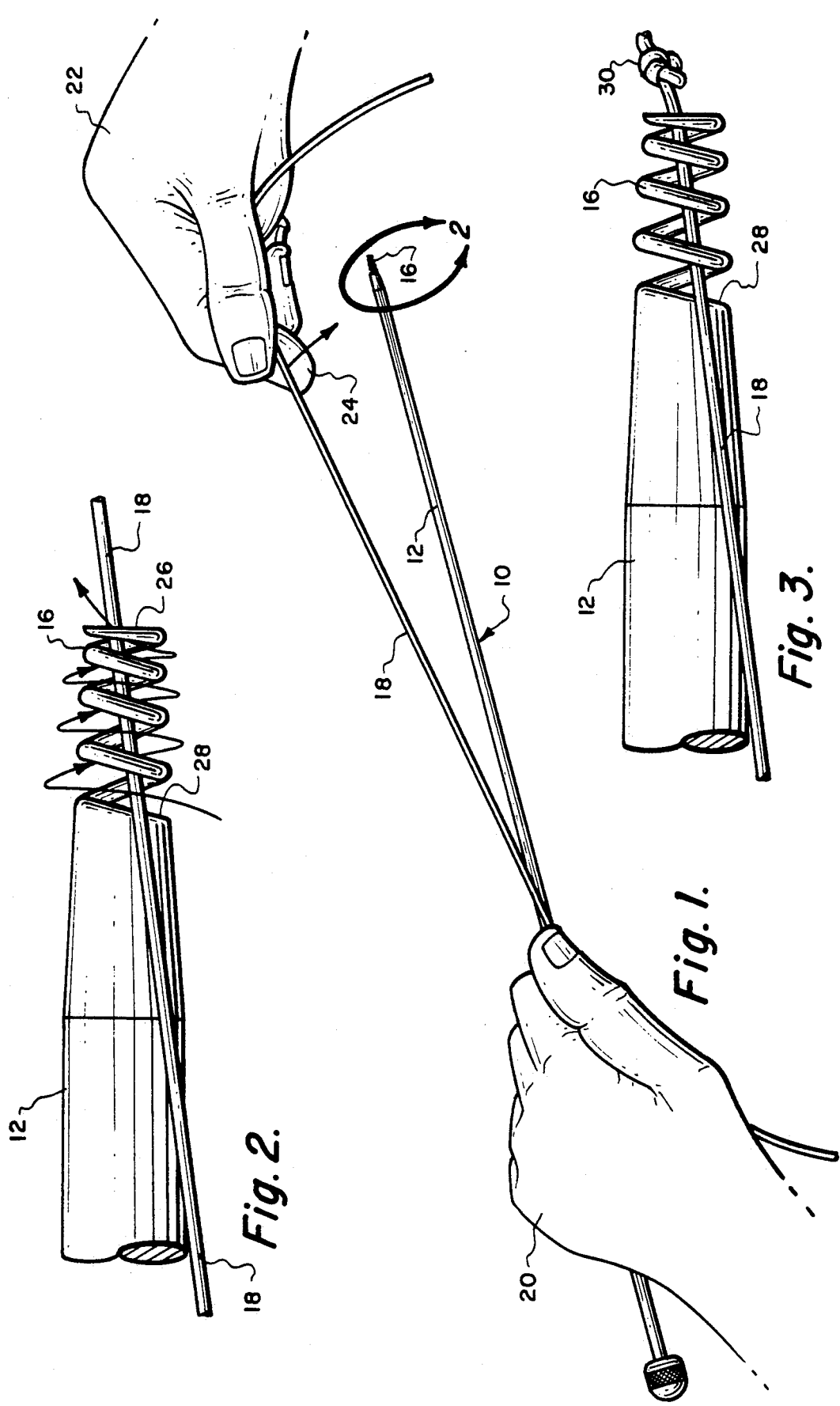

SURGICAL KNOT PUSHING APPLIANCE

FIELD OF THE INVENTION

This invention relates to surgical instruments and appliances and more particularly relates to a surgical knot pushing tool for placement of surgical knots.

BACKGROUND OF THE INVENTION

Often during surgical procedures the surgeon cannot easily reach areas where surgical suturing must be done. In addition it is sometimes difficult to place a surgical knot when suturing because of body fluids which makes the surgical thread slippery and difficult to manipulate. For that reason, a surgical knot pusher is used.

Generally, present surgical knot pushers are comprised of a long shaft having a hook or a v-shaped element on the end for pushing a knot down the surgical thread. These surgical knots are used in places and areas where because of the particular type of surgery, the surgeon may not be able to get his hands or the area is difficult to reach. Places such as bleeders that have been clamped off, are prime targets for use with a surgical knot pusher. The knot is first tied loosely and then pushed down the surgical thread to the site to tie off the particular area being sutured.

A frequent problem with present surgical knot pushers is that the thread slips off the tool during placement of the knot. The fine surgical thread is difficult to handle and is made all the more difficult when made slippery from body fluids. When trying to place a surgical knot it can cause great frustration and anxiety when the thread keeps slipping off the tool while trying to tie the surgical knot. It can be detrimental to the patient for a surgeon to experience such frustration during delicate surgical procedures.

Surgical knot pushers are also useful to increase the efficiency of surgical procedures so that the patient is not kept under anesthesia too long. They are particularly useful in laparoscopic surgery, in which only small incisions are made to reach the area being treated. The area being treated is viewed through a laparoscope while surgical instruments are manipulated through one or two other small incisions. Thus, of course, the area being treated is inaccessible to the surgeon except by use of instruments. There are two ways of tying a knot in a suture during laparoscopic surgery. One way is to tie the knot intra-abdominally or inside the body through instruments and the other is extra-abdominally or outside the body. In the first case, tying the knot is a very delicate procedure requiring lots of experience from the surgeon. There are instruments that somewhat simplify knot tying, but the knot still must be tied using twelve to fourteen inch long instruments while viewing the area on a two dimensional monitor, which is very difficult. In cases when the surgical knot is tied outside the abdomen or body the knot must then be pushed down through a guide tube called a cannula into an abdominal cavity with a tool, such as a knot pusher.

When incisions are made with a special tool called a trocar the sugery is performed through a guide tube called a cannula left in the incision. The trocar is removed and surgical instruments are introduced through a cannula of five, seven or up to ten mm (millimeters). Depending upon the procedure, four to five or more instruments may be used during the surgery. When suturing the surgeon passes the suture and needle through the cannula into the abdomen, sews, brings the end of the suture up through the cannula so that both ends are outside the body, ties the knot and pushes it down through the cannula with a knot pusher.

It would be advantageous if a surgical knot pusher can be provided that would increase the efficiency and ease with which the surgical knots can be placed.

It is therefore one object of the present invention to provide a surgical knot pushing tool that is simple and easy to use.

Yet another object of the present invention is to provide a surgical knot pushing appliance that is reliable and will prevent the knot from easily slipping out of the tool.

Still another object of the present invention is to provide a surgical knot pushing tool having a tip allowing the surgical thread and knot to be easily threaded for use.

BRIEF DESCRIPTION OF THE INVENTION

The purpose of the present invention is to provide a surgical knot pushing tool that is simple and easy to use and which will prevent a surgical knot from easily slipping out of the tool.

The surgical knot pushing tool of the present invention is comprised of an elongate shaft having a handle on one end and a knot placement device on the other end which makes it easy to mount a surgical thread having a knot for placement. The tip of the shaft is provided with a loosely wound spiralling coil terminating in a small hole slightly larger than the largest surgical thread. To mount a surgical thread on the tip, the surgical tool can be held in one hand with a rotating motion applied to the surgical thread with the other. Because of the spiralling coil, threading is simple and easy as the thread will easily slip into the space between adjacent coils. Once in the spiralling coil, the surgical thread will not easily come out except through the opening at the end of the coil. A knot may be tied in the thread and pushed down to a surgical site easily and quickly even through the thread may be slippery from bodily fluids.

In a preferred embodiment of the invention, the spiralling coil is a conical tapered coil tapering down to a small opening at the end that is only slightly larger than the diameter of the thread. The conical coil is preferably relatively rigid to allow the thread to be easily mounted between the coils.

Also, the surgical knot pushing tool can be constructed of a disposable material with the spiralling coil integrally formed on one end and a handle formed on the other. There should be at least three and perhaps four or more coils on the end to allow easy mounting of the surgical thread.

The above and other novel features and advantages of this invention will be more fully understood from the following detailed description and the accompanying drawings, in which:

BRIEF DESCRIPTION OF THE DRAWINGS

FIG. 1 is a perspective view of a surgical knot pushing tool that illustrates the method of mounting the surgical thread.

FIG. 2 is an enlarged view of the tip of the surgical knot pushing tool illustrating the spiralling tapered conical coil.

FIG. 3 is an enlarged view of the tip of the surgical knot pushing tool illustrating an integrally formed spiralling tapered conical coil with a knot in the sugical thread.

DETAILED DESCRIPTION OF THE INVENTION

A surgical knot pushing tool according to the invention is illustrated generally at 10 in FIG. 1 and is comprised of an elongate shaft 12 having knurled handle 14 at one end and spiralling coil 16 at the other end. A surgical thread 18 is mounted on the tool by holding the thread with one hand 20 against the side of shaft 12 and simply rotating thread 18 around the spiral coil tip 16. Pressure applied with the other hand 22 and finger 24 will allow thread 18 to easily slip into a space between adjacent coils of the spiral coil tip.

The spiralling coil 16 on the tip of shaft 12 is conically tapered as shown in greater detail in FIGS. 2 and 3. spiralling Coil 16 has four counter-clockwise spaced apart coils with the end 26 having a hole slightly larger than the surgical thread 18. Preferably there will be at least three to four spirals attached to tip 28 of elongate shaft 12. Elongate shaft can be from 12 to 18 inches long, which would be suitable for most surgical procedures. Longer or shorter or even a telescoping shaft could be used if desired. It is important however, that shaft 20 be substantially rigid to allow positive control of the conically tapered tip 16 for placement of a surgical knot.

FIG. 3 illustrates another enlarged view of the conically tapered spiral coil 16 on tip 28 of elongate shaft 12. However, in this case the conically tapered spiralling coil 16 can be integrally formed on tip 28 of shaft 12. Preferably shaft 12, handle 14 and conically spiraled tip 16 will be made of a substantially homogeneous material such as a durable plastic so that it may be disposable.

Surgical thread 18 is mounted as described in FIG. 1 by placing the thread beneath the thumb of one hand and spiralling the thread against and around the tip 16 until it slips between adjacent coils in conically tapered ccil 16. The knot may be tied before or after mounting surgical thread 18 on knot pushing tool 10. Knot 30 is tied and then placed by pushing tip 28 of elongate shaft 12 into an incision to place the knot at the desired position. The knot may be then tightened to finish the procedure.

This invention is not to be limited by the embodiment shown in the drawings and described in the description which is given by way of example and not of limitation, but only in accordance with the scope of the appended claims.

What is claimed is:

1. A surgical knot pushing tool comprising:
an elongate shaft; handle means on a first end of said shaft; a conically tapered spiralling coil formed on the other end of said shaft, said conically tapered spiralling coil forming an opening that is slightly larger than a surgical thread; whereby a surgical thread may be easily mounted in said conically tapered spiralling coil for placement of a knot by pushing the knot down the surgical thread.

2. The appliance according to claim 1 in which said spiralling coil is integrally formed on the end of said shaft.

3. The appliance according to claim 1 in which said coil makes at least three complete spirals.

* * * * *